(12) United States Patent
Moore

(10) Patent No.: US 6,463,122 B1
(45) Date of Patent: Oct. 8, 2002

(54) MAMMOGRAPHY OF COMPUTER TOMOGRAPHY FOR IMAGING AND THERAPY

(75) Inventor: John Fitzallen Moore, Libertyville, IL (US)

(73) Assignee: Bio-Imaging Resource, Inc., Lincolnshire, IL (US)

( * ) Notice: Subject to any disclaimer, the term of this patent is extended or adjusted under 35 U.S.C. 154(b) by 0 days.

(21) Appl. No.: 09/642,755

(22) Filed: Aug. 21, 2000

(51) Int. Cl.[7] ................................................. A61N 5/10
(52) U.S. Cl. ........................ 378/65; 378/37; 378/64; 378/17
(58) Field of Search .............................. 378/37, 64, 65, 378/17

(56) References Cited

U.S. PATENT DOCUMENTS

| | | | |
|---|---|---|---|
| 3,963,933 A | | 6/1976 | Henkes, Jr. .................... 378/20 |
| 3,973,126 A | | 8/1976 | Redington et al. ............. 378/17 |
| 4,015,836 A | | 4/1977 | Redington et al. ............. 5/601 |
| 4,998,268 A | * | 3/1991 | Winter ........................... 378/63 |
| 5,008,907 A | * | 4/1991 | Norman et al. ................. 378/65 |
| 5,426,685 A | * | 6/1995 | Pellegrino et al. ............. 378/87 |
| 5,548,627 A | * | 8/1996 | Swerdloff et al. .............. 378/4 |
| 5,574,763 A | * | 11/1996 | Dehner .......................... 378/17 |
| 5,583,908 A | * | 12/1996 | Antich et al. .................. 378/65 |
| 5,851,182 A | * | 12/1998 | Sahadevan .................... 600/407 |

OTHER PUBLICATIONS

Toth, et al., "A Dose Reduction X–Ray Beam Positioning System for High–Speed Multislice CT Scanners", pp. 2659–2668 in *Medical Physics*, vol. 27, No. 12, Dec. 2000.

Jorgensen, et al., "Dynamic Image–Adaptive X–Ray Beam limiter", pp. 328–334 in *Biomedical Instrumentation & Technology*, Jul./Aug. 1992.

* cited by examiner

Primary Examiner—David P. Porta
Assistant Examiner—Allen C. Ho
(74) Attorney, Agent, or Firm—Welsh & Katz, LTD.

(57) ABSTRACT

A method and apparatus are provided for irradiating a tumor within a living subject. The method includes the steps of locating the tumor within the living subject, moving a radiation source around the located tumor along a predetermined locus of points having a varying distance between the radiation source and the tumor and steering a radiation beam of the radiation source to irradiate the tumor from each point of the locus of points, where such steering allows the radiation beam to irradiate the tumor at an arbitrary position with respect to the locus of points.

25 Claims, 3 Drawing Sheets

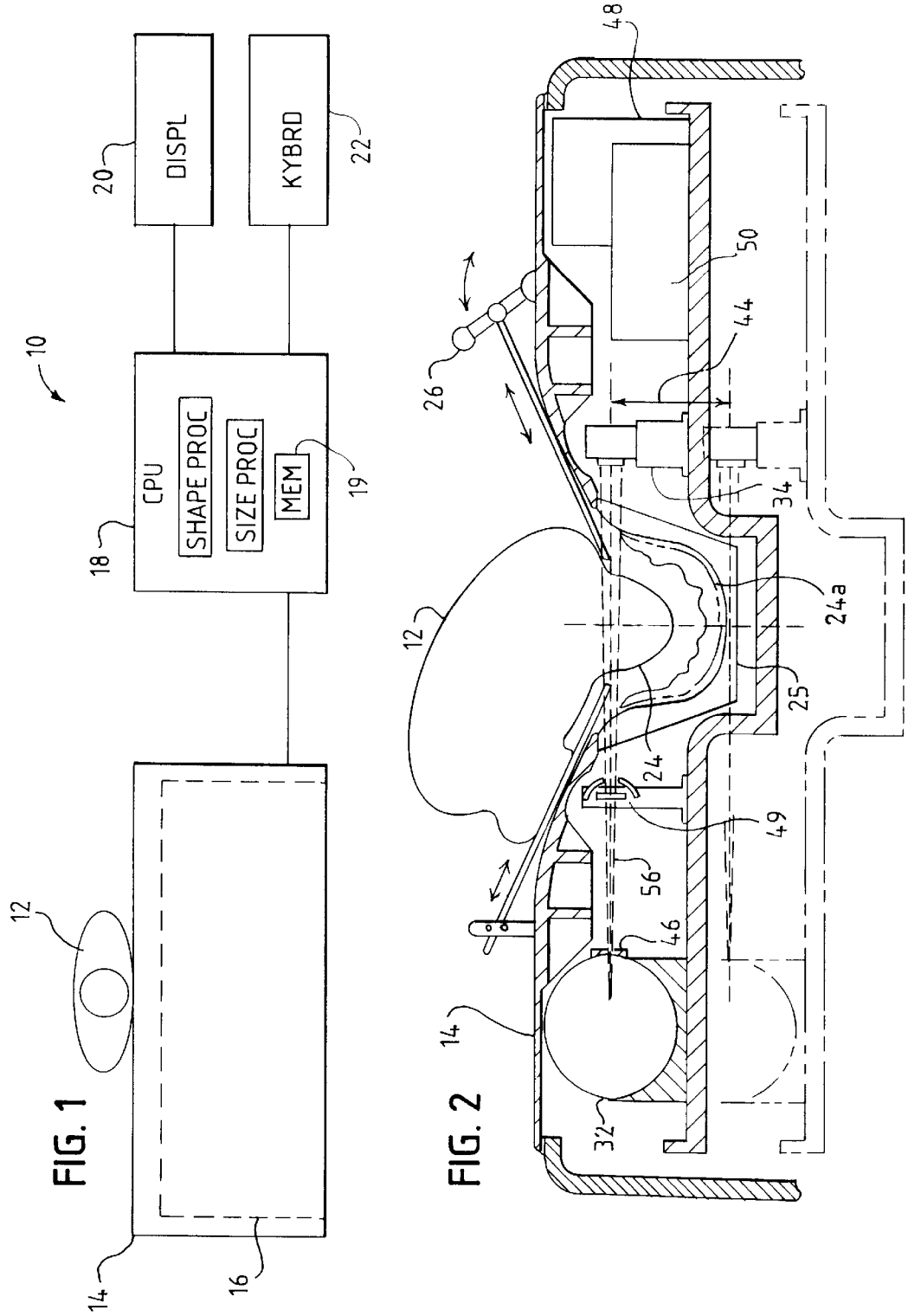

MAMMOGRAPHY OF COMPUTER TOMOGRAPHY FOR IMAGING AND THERAPY

FIELD OF THE INVENTION

The field of the invention relates to x-ray devices and more particularly to x-ray devices capable of both imaging and therapy.

BACKGROUND OF THE INVENTION

X-ray devices used for imaging and/or therapy are known. In the case of imaging, such devices are typically arranged to provide an x-ray source and detector on opposite sides of a body of a patient. The source and detector rotate in unison around the patient collecting x-ray data at discrete locations.

Typically the x-rays are allowed to propagate through the body of the patient in the form of a fan beam. The detectors of a fan-beam device form an array of many individual detector elements, often arranged in the form of an arc to detect x-rays along the spread of the fan beam.

In several scanner models, the x-ray beam is wider in the direction normal to the fan (and may then be referred to as a "cone beam") and is detected by multiple rows of detectors or by a so-called area detector.

In operation, the source and detectors are rotated continuously around the patient, and the signals from the detectors are sampled at intervals of a few milliseconds, so that sets of x-ray absorption profiles are collected at many angular increments around the patient.

From the x-ray data, an associated computer may solve a matrix of equations, or use some other mathematical technique to obtain a measure of the x-ray absorption of each of a number of two-dimensional areas (or "pixels") within a finite thickness of the slice. The pixels may be combined to form a two-dimensional image of a cross-sectional view, or slice, through the patient's body. The patient may then be moved a small distance in a direction normal to the plane of the slice, and the process of x-ray exposure, data collection, and computer data reduction may be repeated to obtain an image of an adjacent slice. The motion and process may be repeated any number of times. Alternatively, the patient may be moved continuously, so that the x-ray beam follows a helical surface within the body. In devices employing a cone beam, several slices may be generated simultaneously.

By associating the data of adjacent cross-sectional slices, a three-dimensional array of data may be obtained. From the three-dimensional array of data, three-dimensional images (or two-dimensional images at orientations different from the slices) can be created, which may be used to determine the location of tumors or other lesions.

Once tumors or other lesions have been identified, the tumor or other lesion may be treated by irradiation. While some, more recent x-ray systems, allow for both imaging and therapy, most x-ray systems do not allow such dual functionality. Further, even where both imaging and therapy are allowed, the effectiveness of such treatments requires careful positioning of the patient to maximize the effectiveness of the therapy on a target tumor or other lesion while minimizing damage to surrounding tissue. Accordingly, a need exists for a device that allows both imaging and therapy that accommodates the vagaries of target location.

BRIEF DESCRIPTION OF THE DRAWINGS

FIG. 1 depicts apparatus for irradiating a tumor in accordance with an illustrated embodiment of the invention;

FIG. 2 depicts a cross-sectional view of one embodiment of the system of apparatus of FIG. 1;

SUMMARY

A method and apparatus are provided for irradiating a tumor within a living subject. The method includes the steps of locating the tumor within the living subject, moving a radiation source around the located tumor along a predetermined locus of points having a varying distance between the radiation source and the tumor and steering a radiation beam of the radiation source to irradiate the tumor from each point of the locus of points, where such steering allows the radiation beam to irradiate the tumor at an arbitrary position with respect to the locus of points.

Movable shutters may be provided on either side of the radiation beam. In this way, a target of a narrow pencil beam of therapeutic radiation no longer has to be centered with regard to movement of the radiation source, and the shutters can be moved in parallel in order to direct the narrow beam to a tumor that is not at the center of rotation. This simplifies patient positioning and allows multiple tumors to be treated without repositioning the patient. This feature also allows the narrow beam to be widened at certain angles to treat tumors that are wider in one dimension than another. It also permits the radiation source to be shut down as it approaches a complete revolution around an irradiated portion of a patient. This is significant, because in prior art devices, the beams at different angles of tilt may coincide at opposite ends of the tilt axis, raising the dose in that direction. Under illustrated embodiments, the shutters can be closed entirely near the axis limits to avoid such problems.

DETAILED DESCRIPTION OF A PREFERRED EMBODIMENT

Figure 3:
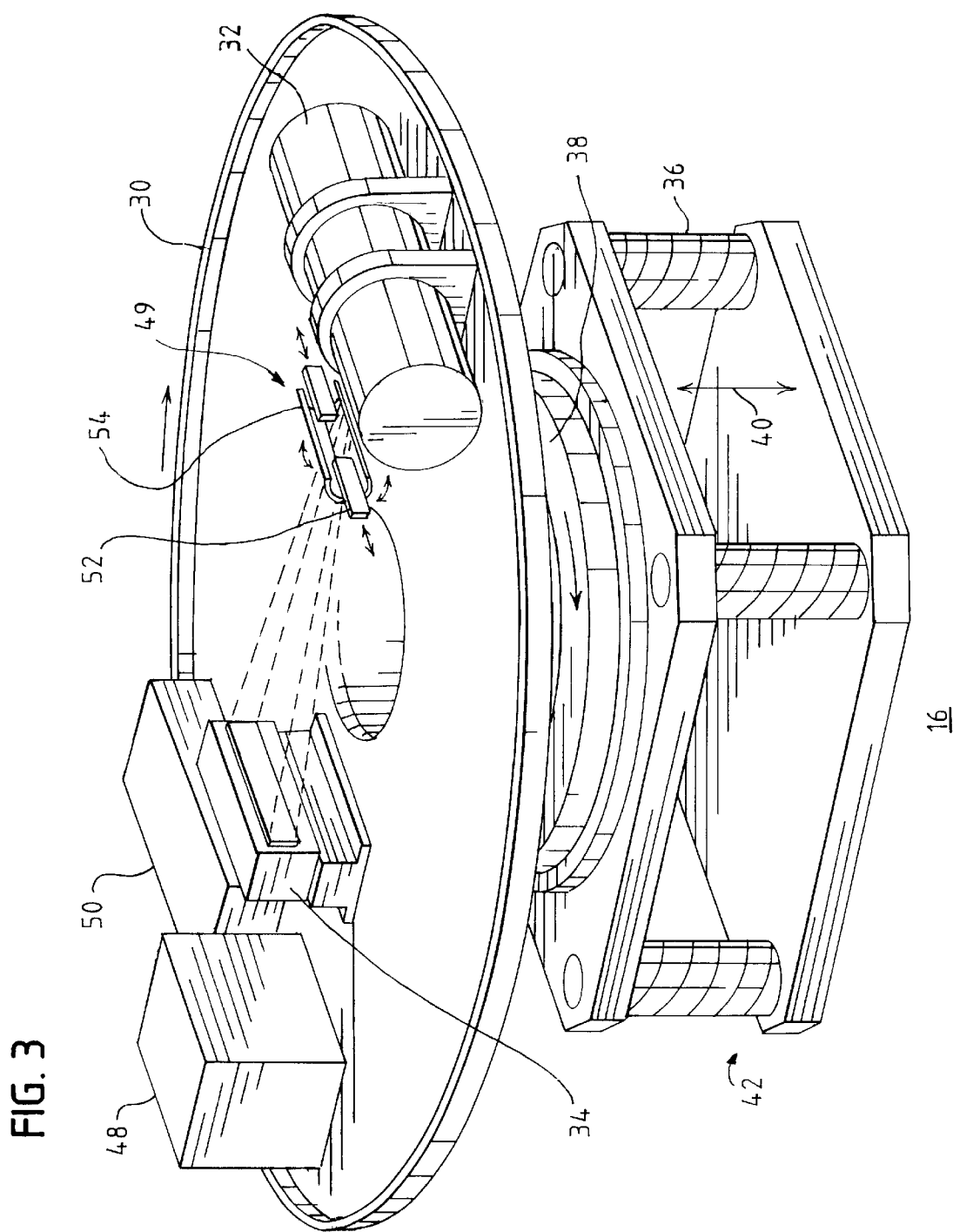
FIG. 3 depicts a perspective view of one embodiment of the apparatus of FIG. 1.

The following text and FIGS. 2 and 3 discuss and illustrate a particular embodiment, that is, application to tomography and therapy of the breast, in which the rotation is around a vertical axis. It should be understood that other embodiments are possible, particularly with respect to conventional whole-body tomography, in which the x-ray source (and, in some but not all designs, the detectors) rotates around a horizontal axis through the body.

FIG. 1 is a block diagram of an imaging and therapeutic x-ray system 10, shown generally in accordance with an illustrated embodiment of the invention. As shown, a patient 12 may be placed upon a patient platen 14. Within the patient platen 14 an xray imaging and therapeutic (x-ray) station 16 functions to form images and provide x-ray therapy to portions of those images (i.e., the patient's body) without the necessity of repositioning the patient 12.

FIG. 2 is a cross-section of the platen 14 and x-ray station 16 of FIG. 1. As shown, a portion of the patient's body 24 (e.g., a breast) is allows to project through the platen 14. A self-centering control 26 is provided for adjusting a width of the breast opening.

Below the platen 14 is the x-ray imaging and therapeutic station 16 (a perspective view is shown in FIG. 3). Within the x-ray station 16, a rotating assembly 30 is provided for support of an x-ray source 32 and x-ray detector 34. The rotating assembly 30 is supported by a rotating bearing 38 and a base 42. The base 42, in turn, is provided with a set of elevator drives 36 that may be used to raise and lower 40 the rotating table. The elevator drives 36 allow a center of the x-ray beam (FIG. 2) to have a vertical travel 44 of from just below the platen 16 to a position of up to 6–½ inches below the platen 16. In conventional whole-body tomography, an equivalent motion is provided by advancing the couch on which the patient lies.

Included on the rotating table 30 is a high-voltage power supply 49 and a set of batteries 50. The power supply 49 and batteries 50 may be provided as a source of power for the x-ray tube 32. They may be located on an opposing side of the table 30 to counterbalance the weight of the tube 32. Alternatively, low-voltage power may be supplied by slip rings instead of batteries.

In operation, x-rays 56 from the tube 32 first pass through a precollimator 46 and then through a controllable set of horizontal and vertical collimators 48. From the horizontal and vertical collimators 48, the x-rays 56 pass through the portion 24 before encountering the detector 34.

The horizontal and vertical collimators 48 (FIG. 3) include a set of left and right horizontal-motion pencil-beam shutter blades 52 and a set of upper and lower vertical-motion slice collimator blades 54. For simplicity, guides and motors are not shown for the two sets of blades 52, 54.

Under an illustrated embodiment of the invention, the horizontal and vertical collimators 48 allow a size and shape of the x-ray beam 56 to be changed and for the x-ray beam to be steered. The ability to control size and shape and to steer the x-ray beam 56 has important implications with regard to patient comfort and to the effects of x-ray therapy.

For example, as a first step, preceding x-ray therapy, the left and right horizontal-motion pencil beam shutter blades 52 may be opened up to provide a fan beam x-ray pattern for imaging. The upper and lower vertical-motion slice collimator blades 54 may be held to a relatively narrow width for fan beam CT imaging. Alternatively, the upper and lower vertical-motion slice collimator blades 54 may also be opened up for cone beam computer tomographic (CT) imaging.

It is contemplated that each of the left and right collimator blades 52 and the upper and lower collimator blades 54 would be provided with an independent drive motor controlled by the CPU 18. Alternatively, the left and right collimator blades 52 may be provided with an opening and closing motor and a separate traversing motor, controlling left and right movement. Similarly, the upper and lower collimator blades 54 may be provided with individual drive motors or with a single opening and closing motor drive and a separate drive motor to allow steering in the vertical direction.

A type of collimator made up of many thin independently driven vanes, called a "multi-leaf collimator" is well known in the field of radiation therapy. However, such multi-leaf collimators are mounted centrally, so that the therapy devices employing them must place the patient so that the tumor is at the center of rotation of the device. It is a teaching of this invention that the entire multi-leaf collimator may be moved away from center (i.e., have a varying distance from the tumor) by a separate computer-controlled motor so that it may always point at an off-center tumor by changing its position and direction of radiation continuously during motion of the x-ray source.

To collect data, rotation of the rotating table 30 may be started, the x-ray tube 32 activated by applying an ortho-voltage to the x-ray tube 32 and successive sets of fan beam data may be detected by the detector array 34. The process may be repeated until the table has traveled the number of degrees required for a first cross-section of data. The data may be collected by the central processing unit (CPU) 18 and stored in a memory 19.

After collection of the first cross-section of data, the elevator drives 36 may be activated to change an elevation of the x-ray beam 56 with regard to the portion 24. The process may be repeated to collect successive cross-sections of data. The process of collecting cross-sections of data may be repeated until sufficient data has been collected (in this case to look for tumors in a breast 24).

Under the illustrated embodiment, collection of data may be accomplished continuously, without stopping at each data point. The scanning system 16 may function by g scanning about a vertical axis perpendicular to the chest of the patient 12, rotating around the pendant breast 24 of a prone patient 12 with a horizontal cone beam for 3-dimensional volume CT. In effect, the table 30 may rotate in a continuous manner, while at the same time, the elevator drives 36 also cause a continuous change in elevation. The result is a helical scan which shortens scan time and thus reduces movement artifacts, compared to separate CT slices. Beam-hardening effects may be reduced through the use of water-equivalent cylinders 25 with cup indentations to complement breast size. This modulates the beam at the breast for lower dosage at the tip. Breast compression is not required.

Once the data has been collected and stored in memory 19, the CPU 18 may begin processing the data into images (e.g., using convolution backprojection algorithms, ART (arithmetic reconstruction), or other well-known techniques) for display on the image display 20. The images may be created and displayed in a conventional manner. A keyboard 22 may be provided to control the physical portion of the breast 24 displayed.

Upon occasion, a tumor 60 (FIG. 4) may be detected within the display 20. The tumor 60 may be visually detected and a periphery manually identified or edge detection software within the CPU 18 may be used to delineate the tumor 60. Any of a number of different methods may be used to identify a size and shape of the tumor 60 (e.g., as described by K. Doi, M. L. Giger, R. M. Nishikawa, K. R. Hoffman, H. MacMahon, R. A. Schmidt "Potential Usefulness of Digital Imaging in Clinical Diagnostic Radiology: Computer-aided Diagnosis", J. Dig. Imaging 8,2–7, 1995; H. Yoshida, K. Doi "Computer-aided Diagnosis in Sonography, Chest Radiography, and Mammography Based on Wavelet Transforms", Int'l Meeting on Nuclear Energy in Medicine, Hanoi, Mar. 29–30, 1999, etc.).

Once a tumor 60 is identified, it may be immediately irradiated or a detected image may be stored in memory 19 for monitoring purposes. Where immediate irradiation is used, a set of machine coordinates may be used as a basis for irradiation. Such immediate irradiation is possible because of the short time period between detection of the tumor 60 and irradiation. With a short time period, the patient 12 is less likely to have moved to any significant degree, nor will it be necessary to reposition the patient on a different device, as is required when detection and therapy are separate. With the low likelihood of movement associated with short time intervals, it may be possible to use a set of coordinates associated with the image previously established to direct subsequent irradiation.

Where an image file is stored for later comparative purposes, a tumor 60 may be located by image registration (e.g., R. Sivaramakrishna "Breast Image Registration Using a Textural Transformation", Ph.D. Thesis, Dept. of Elec. & Computer Eng'g, Univ. of Manitoba, 1997). Where image registration is used, a previously detected image may be located using image registration and a size and shape identified and converted to machine coordinates as discussed above.

To effect irradiation, the system 10 must be able to accommodate the fact that the tumor 60 may not be at a center of rotation (i.e., an isocenter) of the x-ray source 32. Such an assumption is consistent with the random nature of tumor formation and the ability of the system 10 to accommodate such off-center operation. Since the tumor 60 would not be at the center of rotation of the source 32, it is necessary that the x-ray beam 56 be steered to intersect the tumor 60 as the source 32 travels around the tumor 60 during irradiation.

Further, most tumors 60 are not perfectly symmetric. To reduce damage to surrounding tissue, the collimators 48, under control of the CPU 18 change a size and shape of the beam 56 during irradiation to conform to an overall shape of the tumor 60.

The radiation dose to the tumor 60 may be enhanced by the use of contrast agents selectively metabolized by the tumor 60 and hence not present in surrounding tissue. A combination of rotation and tilt may be used to spread the incident radiation dose over a wide area, thereby minimizing skin damage.

Figure 4:
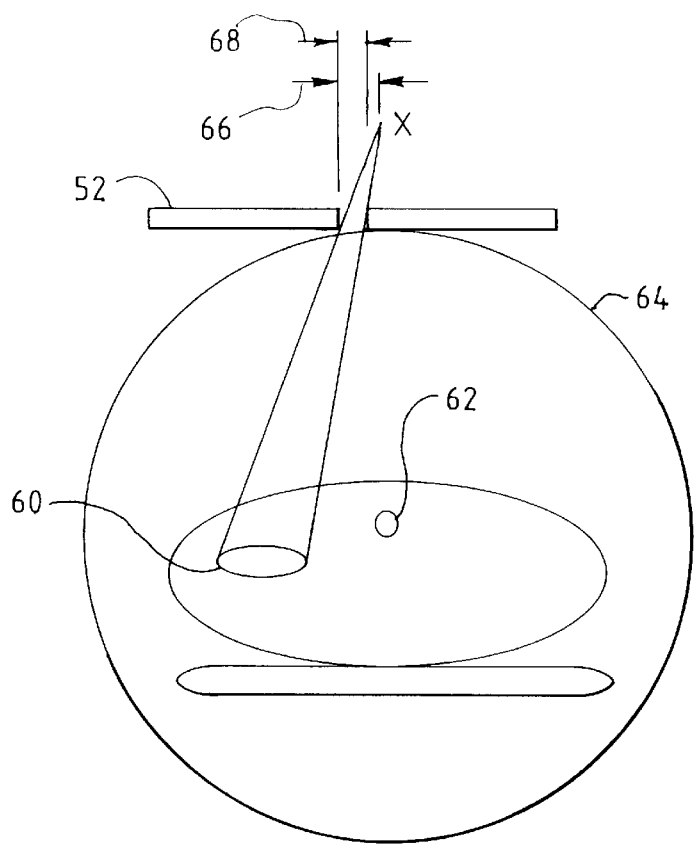
FIG. 4 depicts a view of the irradiation process used by the system of FIG. 1.

FIG. 4 depicts a tumor 60 located to one side of the isocenter 62 of the x-ray projection system 16. For purposes of explanation, it may be assumed that FIG. 4 is a top view in the case of a mammography CT scanner rotating around a vertical axis, or an end view in the case of a conventional CT scanner rotating around a horizontal axis.

In the example of FIG. 4, the tumor 60 is located to the left of the isocenter 62 of the source 32. To allow the x-rays 56 to irradiate the tumor 60, the left and right horizontal-motion pencil beam shutter blades 52 are both moved to the left to steer the beam 56 into the tumor 60. Further, the size of the opening between the shutter blades 52 is adjusted for the diameter of the tumor 60 from that perspective.

To accomplish control of the shutter blades 52, the CPU 18 first identifies a relative location of the tumor 60 relative to a predetermined locus of points 64 around which the source 32 will travel. From each point of the locus of points 64, an angle is determined between a line from the source 32 to the isocenter 62 and a line from the source 32 to the tumor 60. A distance from the source 32 to the tumor 60 may also be calculated. Finally, a diameter of the tumor 60 from that point of the locus of points 64 is calculated.

Using the angle and distance, an offset 66 may be calculated for the shutter blades 52. A aperture size 68 may also be determined based upon a distance of the tumor 60 from the aperture and also the tumor size 60 from that point of the locus of points 64.

Figure 5:
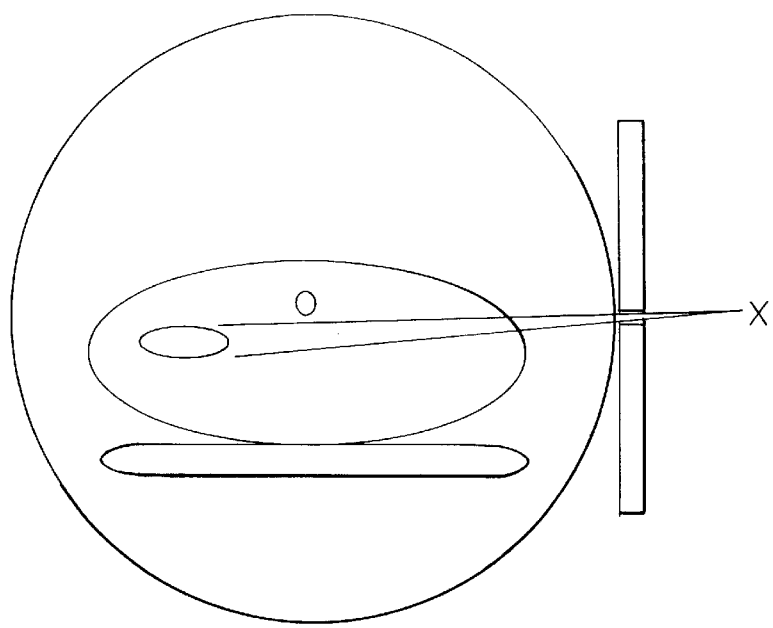
FIG. 5 depicts a view of the irradiation process used by the system of FIG. 1 from another position along the locus of points.

FIG. 5 depicts the process of beam steering from another point along the locus of points. As shown in FIG. 5, the size of the tumor 60 from this location is much smaller and the aperture has been closed considerably. Further, the offset of the tumor 60 from the isocenter is considerably less than in FIG. 4, and it is in the opposite direction. Accordingly, in this case the shutter blades 52 have been moved to a more closed state and the shutter blade set 52 is now offset to the right, instead of the left.

The same process may also be used for the upper and lower vertical-motion slice collimator blades 54. In this case, as the beam 56 approaches the tumor 60 (as the elevator drives 36 move up or down), the beam 56 is directed upwards or downwards depending upon the direction of the tumor 60 from the vertical elevation of the locus of points 64. Further, the size of the aperture of the blades 54 is calculated based upon a distance of the tumor 60 from the source 32 and also a size of the tumor 60 from the perspective of the current point of the locus of points 64.

A specific embodiment of a method and apparatus for irradiating a tumor according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. A method of irradiating a tumor within a living subject, such method comprising the steps of:

locating the tumor within the living subject lying face-down on a patient platen;

during a first time period moving a radiation source around the located tumor along a predetermined locus of points having a varying distance between the radiation source and the tumor and where the predetermined locus of points lie substantially in a horizontal plane;

steering a radiation beam of the radiation source to irradiate the tumor from each point of the predetermined locus of points during the first time period, where such steering allows the radiation beam to irradiate the tumor without the tumor being located at an isocenter of the locus of points;

tilting the locus of points during a second time period so that the locus of points lies in a second plane different from the horizontal plane; and steering the radiation beam of the radiation source to irradiate the tumor from each point of the tilted locus of points during the second time period, where such steering allows the radiation beam to irradiate the tumor without the tumor being located at an isocenter of the locus of points.

2. The method of irradiating the tumor of claim 1 further comprising variably adjusting a size of the radiation beam to substantially equal a projected size of the tumor as seen from each point along the locus of points.

3. The method of irradiating the tumor of claim 1 further comprising variably adjusting an overall shape of the radiation beam to substantially equal a projected shape of the tumor as seen from each point along the locus of points.

4. The method of irradiating the tumor of claim 1 further comprising utilizing a megavoltage radiation source.

5. The method of irradiating the tumor of claim 1 further comprising utilizing an orthovoltage radiation source.

6. The method of irradiating the tumor of claim 1 further comprising imaging the tumor using the radiation source.

7. The method of irradiating and locating the tumor of claim 1 wherein the step of locating the tumor further comprises expanding the radiation beam into a cone beam.

8. The method of irradiating the tumor of claim 1 wherein the step of locating the tumor further comprises rotating the radiation source around the living subject along a locus of points substantially forming a circle.

9. An apparatus for irradiating a tumor within a living subject, such apparatus comprising:
   means for locating the tumor within the living subject;
   means for moving a radiation source around the located tumor along a predetermined locus of points having a varying distance between the radiation source and the tumor during a first time period where the predetermined locus of points lies substantially within a horizontal plane;
   means for tilting the locus of points during a second time period so that the locus of points lie in a second plane different from the horizontal plane; and
   means for steering a radiation beam of the radiation source to irradiate the tumor during the first and second time periods from each point of the locus of points, where such steering allows the radiation beam to irradiate the tumor without the tumor being located at an isocenter of the locus of points.

10. The apparatus for irradiating the tumor of claim 9 further comprising means for variably adjusting a size of the radiation beam to substantially equal a projected size of the tumor as seen from each point along the locus of points.

11. The apparatus for irradiating the tumor of claim 9 further comprising means for variably adjusting an overall shape of the radiation beam to substantially equal a projected shape of the tumor as seen from each point along the locus of points.

12. The apparatus for irradiating the tumor of claim 9 further comprising means for utilizing a megavoltage radiation source.

13. The apparatus for irradiating the tumor of claim 9 further comprising means for utilizing an orthovoltage radiation source.

14. The apparatus for irradiating the tumor of claim 9 further comprising means for imaging the tumor using the radiation source.

15. The apparatus for irradiating and locating the tumor of claim 9 wherein the means for locating the tumor further comprises means for expanding the radiation beam into a cone beam.

16. The apparatus for irradiating the tumor of claim 9 wherein the means for locating the tumor further comprises means for rotating the radiation source around the living subject along a locus of points substantially forming a circle.

17. The apparatus for irradiating a tumor of claim 9 further comprising means for supporting a portion of the living subject in a center of rotation of the radiation source.

18. An apparatus for irradiating a tumor within a living subject, such apparatus comprising:
   a display adapted to locate the tumor within the living subject;
   a rotating assembly adapted to move a radiation source around the located tumor during a first time period along a predetermined locus of points having a varying distance between the radiation source and the tumor and where the predetermined locus of points lie substantially within a horizontal plane;
   an elevator adapted to tilt the rotating assembly during a second time period so that the locus of points lie in a second plane different than the horizontal plane; and
   a set of collimator blades adapted to steer a radiation beam of the radiation source during the first and second time periods to irradiate the tumor from each point of the locus of points, where such steering allows the radiation beam to irradiate the tumor without the tumor being located at an isocenter of the locus of points.

19. The apparatus for irradiating the tumor of claim 18 further comprising a size processor adapted to variably adjust a size of the radiation beam to substantially equal a projected size of the tumor as seen from each point along the locus of points.

20. The apparatus for irradiating the tumor of claim 18 further comprising a shape processor adapted to variably adjust an overall shape of the radiation beam to substantially equal a projected shape of the tumor as seen from each point along the locus of points.

21. The apparatus for irradiating the tumor of claim 18 further comprising a megavoltage radiation source.

22. The apparatus for irradiating the tumor of claim 18 further comprising an orthovoltage radiation source.

23. The apparatus for irradiating the tumor of claim 18 further comprising an image processor adapted to image the tumor using the radiation source.

24. The apparatus for irradiating and locating the tumor of claim 18 wherein the image processor further comprises a fan beam detector adapted to detect a cone beam from the radiation source.

25. The apparatus for irradiating the tumor as in claim 18 further comprising a platen with a self-centering control for supporting a portion of the living subject in a center of rotation of the radiation source.

* * * * *